US011227677B2

(12) United States Patent
Cahill, Jr. et al.

(10) Patent No.: US 11,227,677 B2
(45) Date of Patent: Jan. 18, 2022

(54) SYSTEMS, DEVICES, AND METHODS FOR IDENTIFICATION AND TRACKING OF OBJECTS

(71) Applicants: William J. Cahill, Jr., Bremen, GA (US); Suzanne C Manley, Bremen, GA (US)

(72) Inventors: William J. Cahill, Jr., Bremen, GA (US); Suzanne C Manley, Bremen, GA (US)

( * ) Notice: Subject to any disclaimer, the term of this patent is extended or adjusted under 35 U.S.C. 154(b) by 0 days.

(21) Appl. No.: 16/401,484

(22) Filed: May 2, 2019

(65) Prior Publication Data

US 2020/0350045 A1 Nov. 5, 2020

(51) Int. Cl.
*G06K 19/06* (2006.01)
*G16H 10/65* (2018.01)

(52) U.S. Cl.
CPC ....... *G16H 10/65* (2018.01); *G06K 19/06028* (2013.01); *G06K 19/06037* (2013.01); *G06K 2019/06253* (2013.01)

(58) Field of Classification Search
CPC ............. G16H 10/65; G06K 19/06028; G06K 19/06037; G06K 2019/06253
See application file for complete search history.

(56) References Cited

U.S. PATENT DOCUMENTS

| | | | |
|---|---|---|---|
| 7,896,239 B2 | 2/2011 | Engel et al. | |
| 9,489,466 B2* | 11/2016 | Costantino | G06F 16/9554 |
| 9,519,724 B2* | 12/2016 | Costantino | G06F 16/9554 |
| 2007/0029377 A1 | 2/2007 | Hinckley | |
| 2011/0119187 A1* | 5/2011 | Heeter | G06Q 20/382 |
| | | | 705/44 |
| 2015/0053759 A1* | 2/2015 | Cahill, Jr | G06F 16/24 |
| | | | 235/380 |

* cited by examiner

*Primary Examiner* — Seung H Lee
(74) *Attorney, Agent, or Firm* — J. T. Hollin, Jr. Attorney at Law, P.C.

(57) ABSTRACT

The concept disclosed is referred is a temporary identification device, or, "TID." The TID comprises essentially, different embodiments of a reproducible layer, the reproducible layer being a pictographic rendering of data, information, colors, and visualization codes pertaining to a specific subject, the subject being animate or inanimate. The medium of the reproducible layer may be, but is not limited to, paper, fabric, synthetic material, or an inked imprint/impression of the data and information integral to the TID. The medium of the reproducible layer is encompassed within, or incorporated onto the TID. In some embodiments, the information embodied within or upon the TID may be transferred directly onto the skin or surface of a subject.

28 Claims, 7 Drawing Sheets

SYSTEMS, DEVICES, AND METHODS FOR IDENTIFICATION AND TRACKING OF OBJECTS

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

BACKGROUND OF THE INVENTION

(1) Field of the Invention

The present invention relates generally to information identifying technology, and more particularly, to a system, device, and method for temporary identification a subject, and application of the same.

The background description provided herein is for the purpose of generally presenting the context of the present inventive concept. The work and advances made by the presently named inventors, to the extent it is described in this background section, as well as aspects of the description that may not otherwise qualify as prior art at the time of filing, are neither expressly nor impliedly admitted as prior art against the present invention.

As electronic systems become more universal, there are ongoing efforts directed to coding and managing data in electronic format. Personal data is no exception. In view of the increasing migration toward electronic storage and management of personal data in various environments, there is a need in the art for continued improvement. Therefore, a heretofore unaddressed need exists in the art to address the aforementioned deficiencies and inadequacies.

The use of examples anywhere in this specification, including examples of any terms discussed herein are for illustrative purposes only, and in no way limits the scope and meaning of the invention or of any exemplified term. Likewise, the inventive concept is not limited to the various embodiments set forth in this specification.

(2) Description of the Related Art, Including Information Disclosed Under 37 CFR 1.97 and 1.98

The following presents references and materials which may bear some similarity to the disclosed inventive concept. Some of the references, which may include patents, patent applications and various publications, may be cited and discussed in the description of this inventive concept. The citation and/or discussion of such references is provided merely to clarify the description of the present invention and is not an admission that any such reference is "prior art" to the inventive concept presented herein. All references cited and discussed in this specification are incorporated herein by reference in their entireties and to the same extent as if each reference was individually incorporated by reference.

U.S. Published Patent Application No. 2007/0029377 A1; (Hinckley, C. Feb. 8, 2007) An apparatus, system, and method are disclosed for identification and tracking. The apparatus includes a receiver guide and an applicator. The receiver guide receives a selected portion, such as a fingernail, of a target subject. The target subject may be a human or an animal. The applicator semi-permanently disposes an identification code on an application surface of the target subject. The identification code includes an encoded identifier of identification information corresponding to the target subject. The described apparatus, system, and method advantageously provide better identification and tracking of identification information for the target subject.

U.S. Pat. No. 7,896,239 B2; (Engel et al; Feb. 1, 2011) A portable personalized tracker card is provided. The tracker card may be a patient tracker card. The tracker card includes a control unit, a memory for storing personal data, an energy supply unit and an electrochromic display for displaying the personal data.

U.S. Published Patent Application #2015/0053759 A1; (Cahill, W., et al; Feb. 26, 2015). A device for identifying a subject, including a tattoo layer and a removable cover. The tattoo layer is attachable onto the subject to form a temporary tattoo, and is formed with a resistant material being adhesive such that the temporary tattoo adheres onto the subject. The removable cover detachably covers the tattoo layer. To generate the device, a user may use a computer system to operate a management software to generate the visualization codes including the identification information of the subject, and to print the visualization codes with the resistant material as the tattoo layer on the removable cover. The tattoo layer includes visualization codes thereon, and the visualization codes include identification information of the subject. The user may use a scanner to scan the visualization codes of the tattoo layer to obtain the identification information of the subject, thus identifying the subject.

BRIEF SUMMARY OF THE INVENTIVE CONCEPT

The developments and disclosures herein are primarily for the purpose of addressing needed improvements in patient identification methods in hospitals and medical facilities. Currently, electronic medical record management systems used in hospitals utilize patient bracelets for identifying patients. Information of the patient may be provided on the bracelets. However, the bracelets are generally loosely attached to the body or the limbs of the patient, and may be easily removed from the patient. For example, the bracelets may be broken due to patient body movement. A patient may also remove the bracelets voluntarily due to discomfort. When the patient is not a human being but an animal, the animal patient may have the tendency to bite on the bracelet such that the bracelet is destroyed or removed from the body of the animal patient.

The primary aspect of the present inventive concept relates to a device for providing temporary identification of a subject. The "subject" may be any living organism, or any inanimate object related to a medical process. In that instance, examples of typical subjects include a patient being treated during a medical process, a body part or dissected tissues of a patient, a corpse, property belonging to a subject, or a medical apparatus or device being used or generated during a medical procedure.

The device disclosed herein is referred to as a "temporary identification device," or, "TID" 100. The TID 100 comprises essentially, different embodiments of a "reproducible layer" 110, the reproducible layer being a pictographic rendering of data, information, colors, and visualization codes 130 pertaining to a specific subject 150.

In various embodiments, the medium of the reproducible layer 110 may manifest as, but is not limited to, (a) paper tape, (b) cloth tape, (c) synthetic material, a tattoo, or an inked imprint/impression of the information integral to the TID 100. These various manifestations are referred to as the "medium" of the reproducible layer 110 which is encompassed within, or incorporated into the TID 100. In some embodiments, the information embodied within or upon the TID 100 may be transferred directly onto the skin or surface of a subject. When used as temporary identification in a medical or patient care environment, the reproducible layer 110 must comprise a medically-approved medium.

The term "subject," 150 when used herein, may be an inanimate object, a human, or an animal. Although various exemplary embodiments of the present invention disclosed herein may be described in the context of using temporary identification renderings for identifying patients, it should be appreciated that aspects of the present inventive concept disclosed herein are not limited to utilization in the medical field. The inventive concept may be practiced in business, industrial, or commercial endeavors in conveying essential information identifying relevant objects or circumstances, without departing from the scope of the disclosures herein.

The present inventive concept relates to temporary devices for identifying a subject 150 where, in the preferred embodiment, the subject is a human. In some embodiments, the TID 100 will preferably include a segment of material containing a reproducible layer 110 which may or may not have a first (outer) surface 112 and a second (interior) surface 114. In some embodiments, the interior surface 114 may be attachable onto the subject so as to temporarily display data and information for identifying the subject. A removable coating 120 may detachably cover the outer surface 112 of the reproducible layer 110. In some embodiments the reproducible layer 110 of the TID 100 may require the application of an adhesive substance such that the reproducible layer 110 adheres onto the subject 150.

In the preferred embodiment, the TID 100 includes certain visualization codes 130 and specific color designations thereon. These visualization codes 130 may vary from subject to subject, dependent upon the designated information essential to the field of endeavor involving the subject. The visualization codes 130, in many embodiments, include Quick Response (QR) 99 codes. QR codes 99 are often associated with a medical patient's electronic record.

For exemplary purposes only, in the field of hospital care, visualization codes, and specific coloring, ranging from most severe to routine care, the color codes indicate as follows:

(a) Black/White is the most severe. This condition could quickly cause the death of the patient.
(b) Any other conditions not as severe would be assigned colors darkest to lightest, indicating decreasing severity.
(c) Conditions could include anything medical professionals would deem important and worthy of prompt medical attention or care.
(d) A border color on the reproducible layer 110 would correspond to the color of a hospital unit to which the patient is assigned. Examples of hospital units include, but are not limited to intensive care, neonatal, pediatric, coronary, cardiothoracic, oncology, and post-anesthesia.

In certain embodiments, the medium used in the TID 100 may be readily and efficiently removed from the subject 150, if necessary, by use of a corresponding chemical solvent. The desired result is such that either the medium of the reproducible layer 110, or the imprint left by the reproducible layer 110, is removable from the subject 150 when dissolved by contact with the chemical solvent. In certain cases, the chemical solvent is alcohol or baby oil.

As necessary, the reproducible layer 110 may include a resistant ink. Further, in some embodiments, the reproducible layer 110 may be formed on the removable coating 120 by printing with the resistant ink. In certain embodiments, the removable coating 120 is transparent or semi-transparent such that the visualization codes 130 of the reproducible layer 110 are discernible through the removable coating 120. The removable coating 120 may be formed from paper, plastic, or other suitable substance.

The visualization codes 130 include at least one of visualization of optical machine readable codes and text codes. In other embodiments, the visualization of optical machine readable codes includes at least one of a bar code and a quick response (QR) 99 code.

BRIEF DESCRIPTION OF THE VIEWS OF THE DRAWINGS AS EXEMPLARY EMBODIMENTS OF THE INVENTIVE CONCEPT

The accompanying drawings illustrate one or more embodiments of the inventive concept and, together with the written description, serve to explain the principles of the invention. Wherever possible, the same reference numbers are used throughout the drawings to refer to the same or like elements of an embodiment.

FIG. 1 shows a stylized front view of a temporary identification device 100 comprising a reproducible layer 110 which contains data, information, and visualization codes for identifying a subject.

FIG. 2 depicts the temporary identification device 100 and reproducible layer 110 being generated from a printer 200 after the printer 200 has received electronic inputs concerning a subject.

Figure 3A:
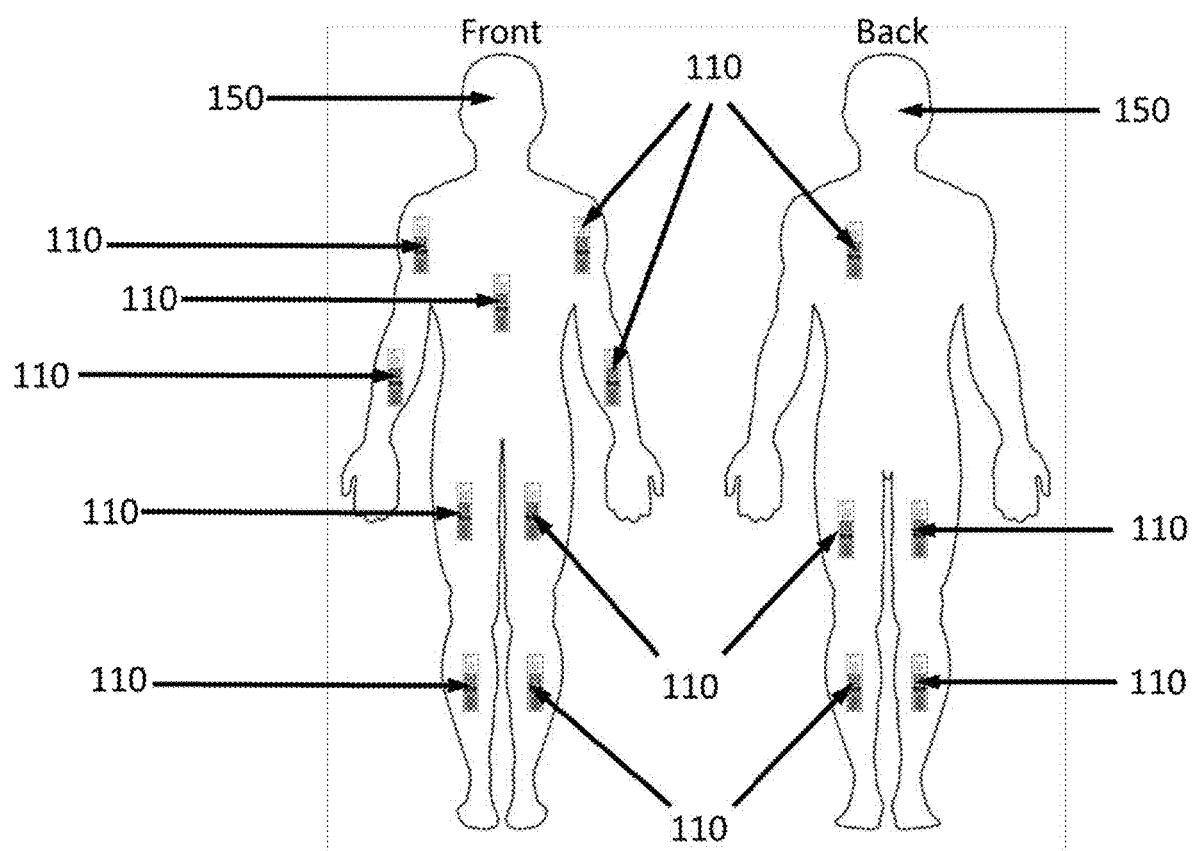
FIG. 3A illustrates a variety of locations on the front and rear of the body of an adult subject 150 upon which the reproducible layer 110 may be transferred or otherwise disposed.
Figure 3B:
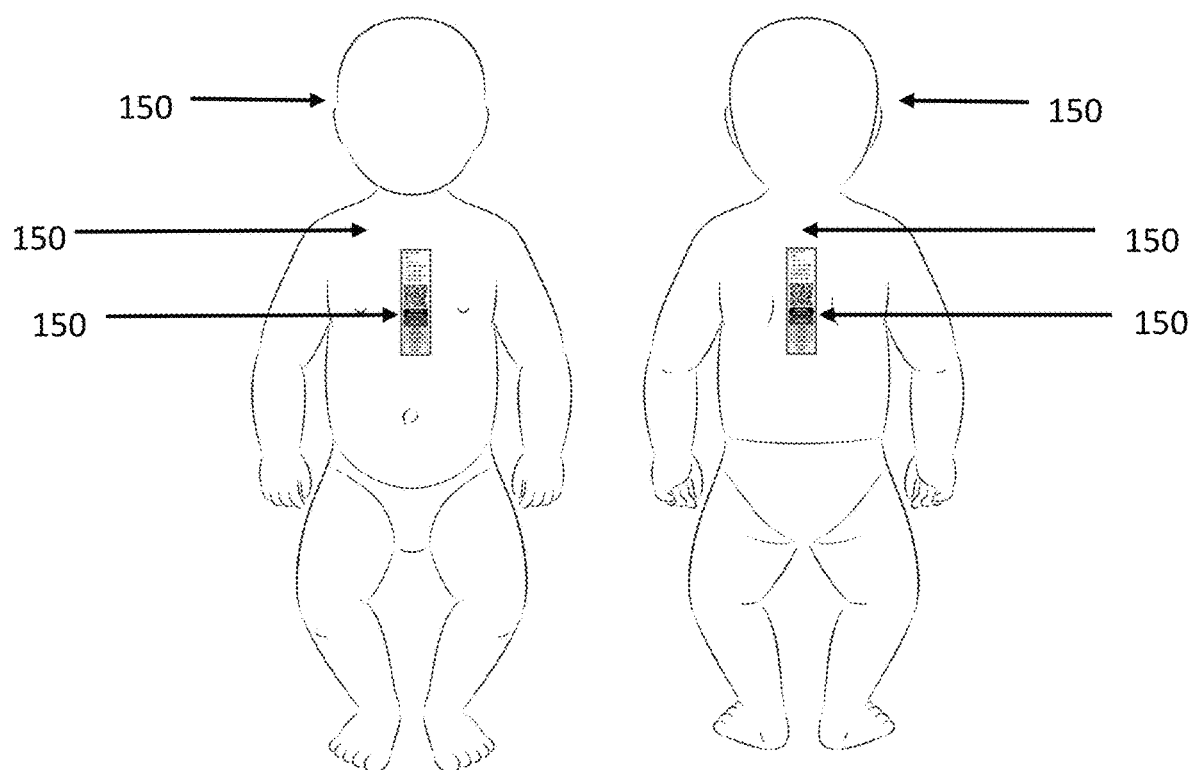
FIG. 3B shows a variety of locations upon an infant or toddler subject 150 upon which the reproducible layer 110 may be transferred or otherwise disposed.
Figure 3C:
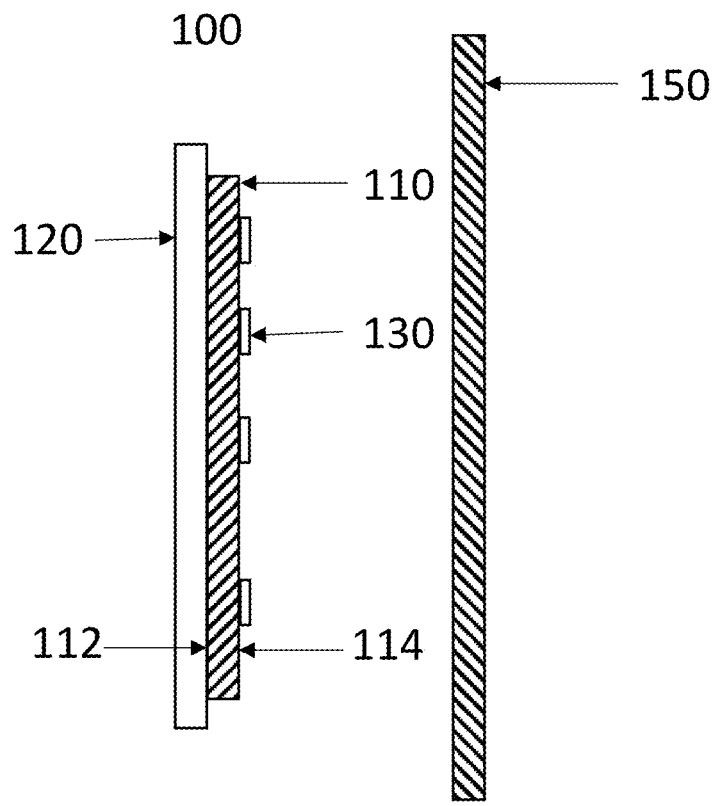

FIG. 3C presents a cross-sectional view of the temporary identification device, including a removable coating 120, the reproducible layer 110, with the visualization codes 130, the outer surface 112, and the interior surface 114.

Figure 4:
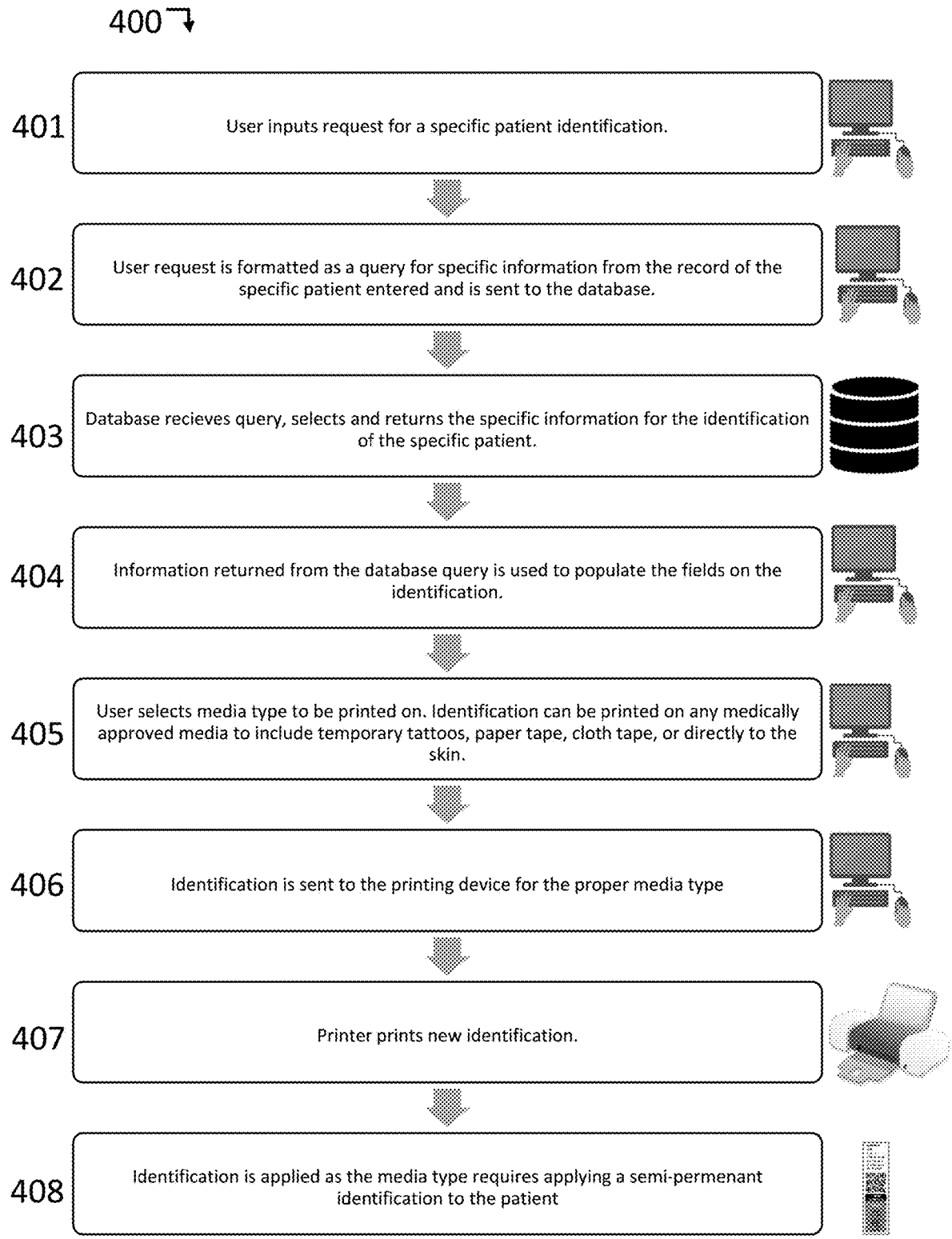

FIG. 4 presents a flowchart 400 setting forth the method (steps 401-408) of acquiring information and preparing the underlying identification relating to a subject 150, according to one embodiment of the present invention.

Figure 5:
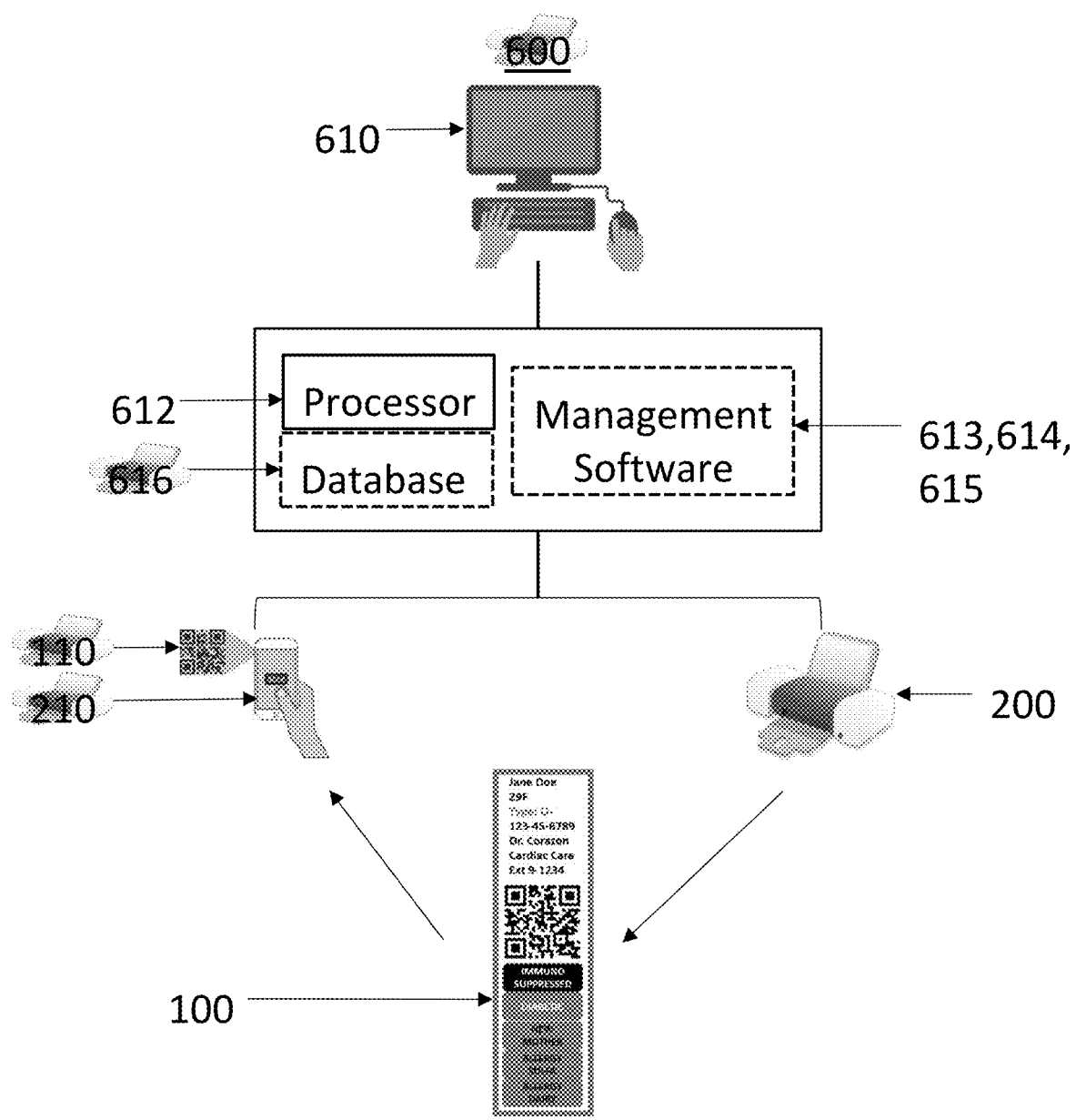

FIG. 5 depicts, schematically, a system 600 for the electronic input of information identifying a subject 150 and the processing and transmittal of such data and information to electronic devices for useable reproduction of the information.

DETAILED DESCRIPTION OF THE INVENTIVE CONCEPT

The objects, features, and advantages of the inventive concept presented in this application are more readily understood when referring to the accompanying drawings, which show exemplary embodiments. This invention may, however, be embodied in many different forms and should not be construed as limited to the embodiments shown in drawings. Rather, these embodiments are provided so that this disclosure will be thorough and complete, and will fully convey the scope of the inventive concept to those skilled in the art. Like reference numerals refer to like elements throughout The term "optical machine readable codes", as used herein, refer to geometric patterns or representations of data which is readable using an optical machine, such as an optical scanner, and corresponding interpretive computer software programs.

The following disclosures are made as to the embodiments of the inventive concept in conjunction with the accompanying drawings in FIG. 1 through FIG. 6. In accordance with the purposes of this invention, as embodied and broadly described herein, the present inventive concept, in different aspects, relates to a system, device and method for identifying a subject.

In certain embodiments, the term, "patient" may refer to a human patient, or may be an animal patient. In certain embodiments, the medical object may refer to, without being limited, medical instruments, medical consumables or disposables, medicines or chemicals and/or their containers, medical waste, or any other medical or clinical related objects in the medical process.

Figure 1:
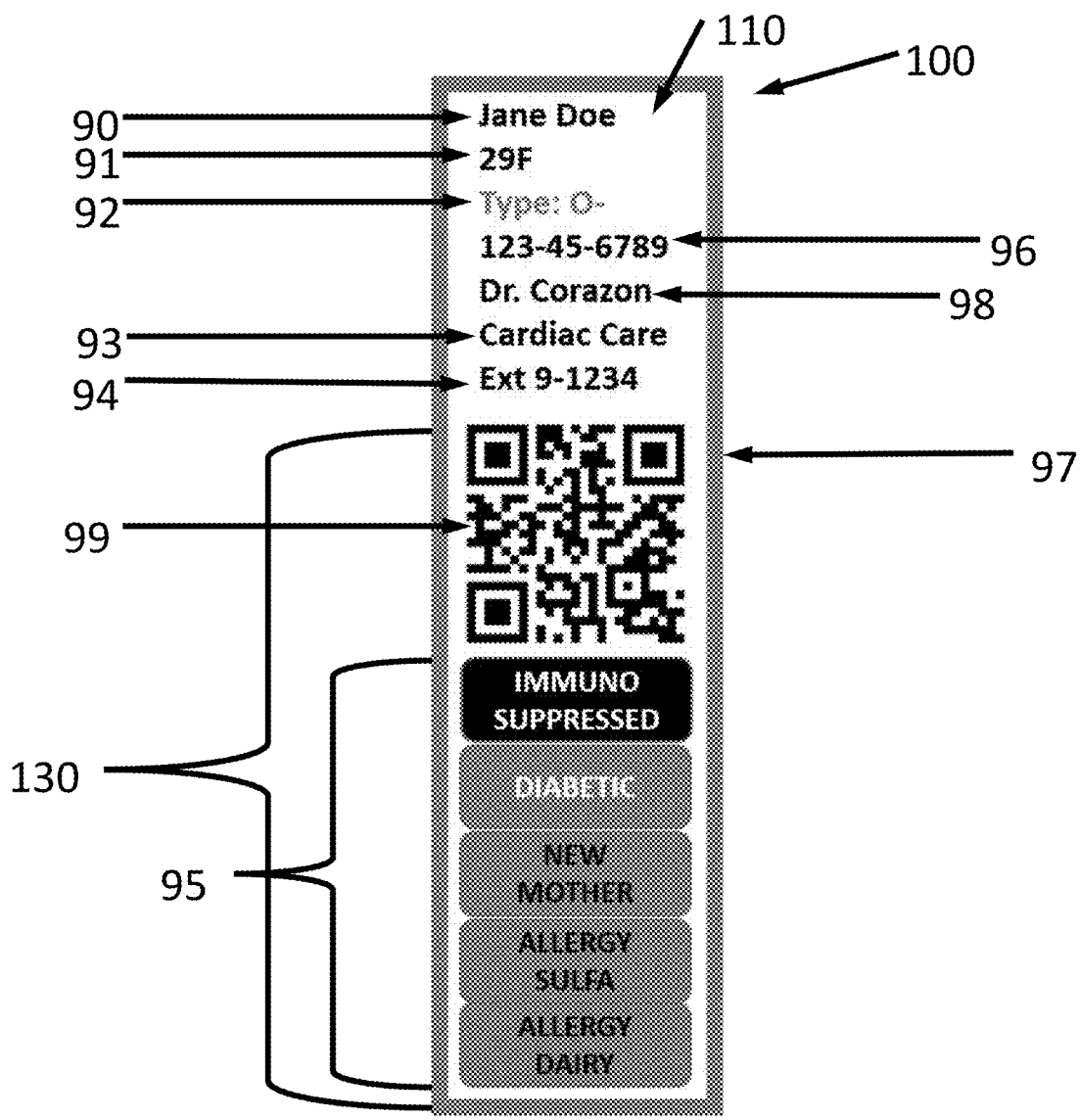

FIG. 1 shows, stylistically, a temporary identification device (TID)) 100 containing information embedded on or within the medium of a reproducible layer 110, which information identifies a subject, according to one embodiment of the present inventive concept. The medium comprising the reproducible layer 110 may be fabric, synthetic material, durable paper, tattoo, or other substance. In this instance, the subject being identified by the TID 100 is a female, age 29.

Figure 2:
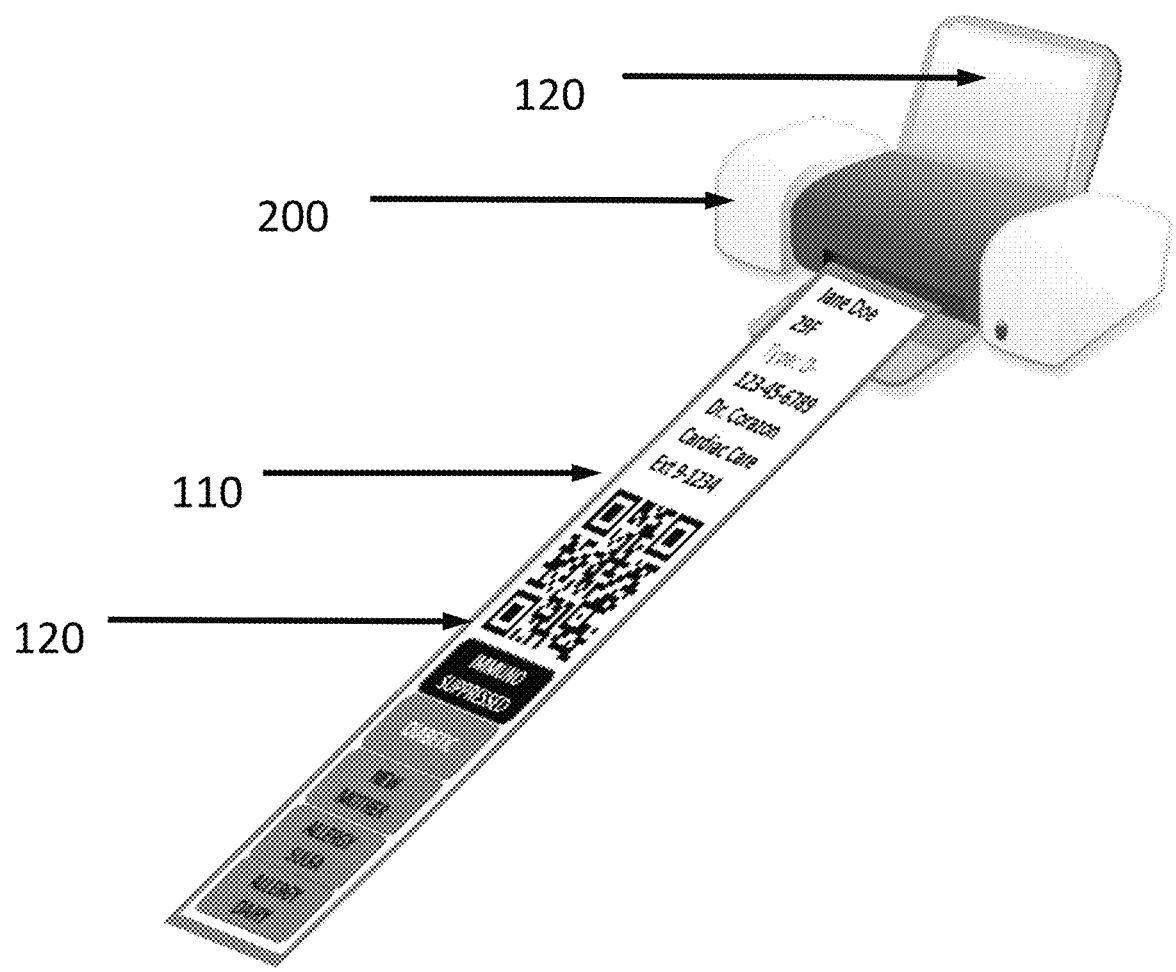

FIG. 2 depicts the printing and production/fabrication of the TID 100. The reproducible layer 110 integral to the TID 100 is a medium containing a summation of information, being relevant data and facts concerning the subject 150. Again, referring to FIG. 1, it is also shown that the device 100 includes a plurality of visualization codes 130/90-99 thereon. In the example shown in FIG. 1, the visualization codes 90-99 provide information that is essential to caregivers treating patients in a hospital or other medical facility. FIG. 2 illustrates that a quantity of removable coating 120 is available for incorporation on a surface of the reproducible layer 110, if required.

In embodiments involving medical or patient care, the visualization codes 90-99 may also include visualization of optical machine readable codes or text codes. As shown in FIG. 1, the visualization codes 90-99 include a quick response (QR) code 99. Specifically, for illustrative purposes, the information may be ascertained from the visualization codes 90-99 that the human patient is "Jane Doe" 90, and is a twenty-nine year old human female 91. The patient, being the subject 150, has a personal identification number 96, 123-45-6789. The QR code 99 is unique for this patient. The QR code 99 is optically readable (i.e., scannable) for retrieval of the identification information of the patient, using corresponding optical machine and corresponding interpretive computer software programs.

The reproducible layer 110 is fabricated so as to enable transfer a temporary impression of relevant information onto the subject 150 for the purpose of identifying the subject 150. Thus, the reproducible layer 110, or the imprint created by the reproducible layer 110 must be capable of adhering to the subject 150 for a certain length of time without being easily removed from the subject 150.

In certain embodiments, the reproducible layer 110 may be formed with an adhesive-type material. The adhesive material facilitates the reproducible layer 110 adhering to the subject 150. Further, the reproducible layer 110 is resistant to water such that the reproducible layer 110 is not easily removable from the subject 150 due to sweat, blood and/or other body fluid that may be generated by the subject 150 during the medical treatment. In other embodiments, the reproducible layer 110 may be a tattoo.

Thus, the reproducible layer 110, when transferred, may stay on the subject as a means of identifying the subject 150. In certain embodiments, the adhesive material or the imprint formed by the reproducible layer 110 may be dissolvable in a specific chemical solvent, such as alcohol or baby oil, or any other organic chemical solvent. Thusly, in the embodiment above described, the reproducible layer 110 is only removable from the subject 150 when using the specific chemical solvent to dissolve the adhesive.

The removable coating 120 is a thin sheet which may be detachably placed in position over the outer surface 112 of the reproducible layer 110. In certain embodiments, the removable coating 120 may be thin enough to be transparent or translucent, such that the visualization codes 90-99 of the reproducible layer 110 are recognizable through the removable coating 120 without the need to detach the removable coating 120. For example, the removable coating 120 may be formed with a piece of transparent/translucent paper or clear plastic. Currently, the Food and Drug Administration (FDA) has approved certain temporary tattoo paper or other materials that can be used as the removable coating 120.

In certain embodiments, the substance forming the reproducible layer 110 may be entirely, or partially, composed of a resistant ink. The resistant ink is applied to the interior surface 114 of the reproducible layer 110. The outer surface 112 of the reproducible layer 110 may be covered with a removable coating 120 for protective purposes. Currently, there are FDA approved inks that may be used as the resistant ink, such as Colorcon® printing inks and other resistant inks.

As stated earlier, FIG. 2 shows schematically production of the device according to one embodiment of the present invention. FIG. 2 shows that a printer 200 may be used to print the TID 100, in juxtaposition with a reproducible layer 110. The printer 200 may be an inkjet printer, a laser printer, or any other type of printers capable of applying the resistant ink or resistant materials onto the removable coating 120 to form the reproducible layer 110.

When the user intends to produce a TID 100 for a subject 150 in a hospitalization or medical facility, the user may first obtain identification information of the subject 150, and then use a computer and corresponding software to generate the visualization codes 90-99, which contain vital information regarding the subject 150. Then, the user may use the printer 200 to print the visualization codes 90-99 onto the reproducible layer 110, or onto the transparent or semi-transparent removable coating 120 with the resistant ink to form the reproducible layer 110. In certain embodiments, the removable coating 120 is also part of the TID 100 production process.

The design of the TID 100, in whatever form, has as its primary objective, the facilitation of transfer of the image or the actual reproducible layer 110 onto a subject 150. When a user intends to apply adhesive-type embodiments of the reproducible layer 110 onto the subject 150, the user disposes the TID 100 on the subject 150, with the outer surface 112 of the reproducible layer 110 in direct contact with the subject 150. Then, the user applies pressure to the TID 100 removable coating such that the interior surface 114 of the reproducible layer 110 is forced to adhere to the subject 150.

In certain embodiments involving health care, the reproducible layer 110 may adhere onto the subject at any location which a caregiver or other concerned person may easily locate for identifying the subject 150.

FIG. 3A illustrates a variety of locations for transfer of the reproducible layer 110, or its imprint, onto the skin surface of an adult human subject 150. For example, the temporary reproducible layer 110 may be placed upon the arms, legs, chest, thigh, or any other exposed body parts of the subject 150. When the subject is an animal patient, the reproducible layer 110 may be placed so as to adhere to the neck, trunk, tail or any other exposed body parts of the animal. When the subject is an inanimate object, the reproducible layer 110 or its imprint may be placed so as to adhere to any exposed part of the object, or may adhere on the container of the object.

FIG. 3B shows the application of the reproducible layer 110 of the TID 100 according to a different embodiment of the present inventive concept. In this embodiment, the subject 150 being identified by the TID 100 is a human baby, or toddler, patient. Thus, the reproducible layer 110 may adhere to the chest 152 or back 153 of the baby, which makes it expedient for nurses or doctors to identify the baby patient. It is understood that the reproducible layer 110 may also be placed so as to adhere to other locations of a toddler's body.

In FIG. 3C there is shown a close-up, cross-sectional view of the TID 100 in close proximity to a subject 150 to which the TID 100 will be applied. It is to be noted that, a user must place the entirety of the TID 100 on the subject 150, with the interior surface 114 of the reproducible layer 110 in direct contact with the subject 150. Then, the user applies pressure to the TID 100 removable coating 120 such that the interior surface 114 of the reproducible layer 110 is forced to adhere to the subject 150. In some embodiments, the interior surface 114 may be attachable onto the subject so as to temporarily display data and information for identifying the subject. Also shown is the visualization codes 130 adhering to the interior surface 114, comprising a resistant ink. A removable coating 120 may detachably cover the outer surface 112 of the reproducible layer 110.

Generally, the data and facts on the reproducible layer 110 may include a variety of information, based on the nature of the subject. For example, when the subject 150 is a human patient, the identification information may include information such as personal data, electronic health record (EHR) data, electronic medical record (EMR) data, or any other information, such as an instruction to the user (e.g. doctors, surgeons or nurses).

When the subject 150 is an animal patient, the identification information may include information of the animal, such as information on the owner of the animal, EHR or EMR of the animal, or any other information related to the animal patient, or medical treatment applied to the animal. Should the subject 150 be a corpse, either human patient or animal patient, the identification information may include information related to the death, such as cause of death and/or death date and time. When the subject 150 is a medical instrument, the identification information may include the name, registration number, manufacturer, and any limitations of the medical instrument.

Where the subject involves medical disposables or medical waste, the identification information may merely include a sign showing "waste". In certain embodiments, the TID 100 may be used for certain instructional or warning purposes involving medical treatment. In this case, the identification information may include instructional, precautionary, or warning text codes or symbols, which is directly recognizable by the user without using a machine.

In some situations, where removal of the reproducible layer 110 or its imprint is desired, it may be necessary to accomplish this by using a chemical solvent in which the reproducible layer 110 is dissolvable. Generally, such chemical solvent should be made unavailable or inaccessible in the environment of the subject 150 so as to prevent accidental or premature removal of the reproducible layer 110. When the subject 150 is a human or animal patient, the chemical solvent should be safe to apply to the skin of the subject 150. For instance, where the chemical solvent is alcohol or baby oil, a user may use alcohol or baby oil to wipe out or rub on the reproducible layer 110 in order to remove it.

Another aspect of the present inventive concept relates to implementing a method for providing identification of a subject. In certain embodiments, the method may be implemented by management software 614 executable on a computer system 600. In certain embodiments, the management software may be an EHR management software system 613 or an EMR management software system 615.

FIG. 4 presents a flowchart setting out the method 400 of identifying a subject 150 according to one embodiment of the present inventive concept. For exemplary purposes only, the method disclosed is applicable to a health care environment, typically a hospital. The same method may also be utilized in other commercial or business applications requiring temporary identification of a subject 150.

In conjunction with the utilization of the disclosed method 400, a specific computerized system 600 (illustrated in FIG. 5) is placed into operation. A user inputs into a computer 610, which accesses a processor 612, queries concerning a subject 150. In response, the database 616 communicates with the system 600 database 616 (ref. FIG. 5) and returns information concerning the subject 150.

As further clarification, at step 401, FIG. 4, a user (by way of example only, a doctor, a surgeon, or a nurse) sets out requests to obtain specific information on a subject. The requests must be formatted and electronically entered into the database of a management system, such that the management software 613, 614, 615 receives the identification information of the subject 150.

Method for Identifying the Subject

As further explanation of the primary aspect of the present inventive concept, the method for identifying a subject is described as follows:

(a) receiving identification information on the subject 150;

(b) generating visualization codes 130 including the identification information of the subject 150;

(c) printing the visualization codes 130 with a resistant ink onto a reproducible layer 110 form a identification of the subject 150, where the resistant ink may be adhesive such that the reproducible layer 110 is capable of adhering onto the subject 150;

(d) at a later stage, and as necessary, scanning the reproducible layer and receiving a corresponding scanning signal, where the received scanning signal contains the identification information of the subject 150;

(e) retrieving the identification information of the subject 150 from the received scanning signal; and (f) enabling a computer system 610 to search for the information of the subject 150 stored in the system 610 database 616;

As discussed above, the identification information sought relating to a subject 150 may include different data and facts based on the nature of the procedure or circumstances. For example, when the subject is a medical patient, the user may first contact the patient, and obtain necessary information for identification of the patient. In certain embodiments, when the user acquires, organizes, and transmits patient information using a computer having an E-IR 613 or EMR 615 management system, the user may obtain the information based on the regular procedure currently used in the EHR 613 or EMR 615 management system.

After the user's queries are received by a computer 610, at step 402, the system database 616 may operate the software 614 to generate the visualization codes 130, including the identification information of the subject. In certain embodiments, the visualization codes 130 may include one or both of visualization of machine readable codes (e.g., the bar code 132, the QR code 99, or other machine readable codes) and text codes. In practice, the user may use a computer having the EHR 613 or EMR 615 management software to enter the information of the patient, and the EHR 613 or EMR 615 management software may generate the visualization codes 130, including the identification information of the patient.

Then, at step 406, the user may operate the EHR or EMR management software 613*b*, 615 to print the visualization codes 130, preferably with a resistant ink as a reproducible layer 110, or on a removable coating 120 to thereby form a temporary identification device 100 pertaining to the subject. The reproducible layer 110 would also include the visualization codes 130 thereon.

Further, in practice, the user may access the database 616 to control a printing device, such as a printer 200, or a handheld device 210 to print or display the reproducible layer 110. This is illustrated in step 407 of the method, and also in FIG. 5.

In certain embodiments, a removable coating 120, which may be a thin sheet of appropriate material, may be detachably placed in position over the outer surface 112 of the reproducible layer 110. This removable coating 120 may be thin enough to be transparent or translucent, such that the visualization codes 90-99 on the reproducible layer 110 are discernible through the removable coating 120 without the need to detach the removable coating 120. For example, the removable coating 120 may be formed with a piece of transparent/translucent paper or clear plastic.

At step 408 of the disclosed method 400, the user may form the reproducible layer 110 onto the subject by use of the temporary identification device 100. FIG. 4 shows a flowchart 400 for the process of transferring the data and information contained on the reproducible layer 110 onto the subject 150 according to one embodiment of the present inventive concept. Specifically, the transferring of the temporary identification may include those actions set forth at step 408: the user disposes the reproducible layer 110 onto the subject 150 with the interior surface 114 of the reproducible layer 110 in direct contact with the skin/surface of the subject 150.

This transfer may be accomplished by the user applying pressure to the removable coating 120 of the device toward the subject 150 such that the reproducible layer 110 or its imprint adheres onto the subject 150 to form a temporary identification. Optionally, also at step 408, the user may detach the removable coating 120 from the reproducible layer 110. In certain embodiments, as long as the removable layer 110 adheres onto the subject 150 properly, the visualization codes 130 of the reproducible layer 110 may be readable for identifying the subject 150 regardless of whether the removable coating 120 is detached or not.

In certain embodiments, the removable coating 120 may be transparent or semi-transparent such that the visualization codes 130 are discernible through the removable coating 120. Accordingly, as long as the scanning process is performed properly, the scanning signal should include the identification information of the subject 150, which is recognizable by the management software.

Once the reproducible layer 110 is formed on the subject 150, at step 408 it is shown that other personnel or newly arriving caregivers may scan the reproducible layer 110 on the subject and receive a corresponding scanning signal. Specifically, the new caregiver may use an optical scanning device, such as a scanner, handheld device, or other compatible scanning device, to scan the visualization codes 130 (e.g., items 90-98 depicted in FIG. 1) or the QR code 99) on the reproducible layer 110 to receive the scanning signal.

The newly arriving personnel may then be informed enough to make key decisions in the care of the subject 150. In other embodiments of the inventive concept, a user may scan the reproducible layer 110 adhering to a subject and acquire information relevant to the immediate needs of a subject 150.

In certain embodiments, the removable coating 120 may be transparent or semi-transparent such that the visualization codes 130 are discernible through the removable coating 120. Accordingly, as long as the scanning process is performed properly, the scanning signal should include the identification information of the subject 150, which is recognizable by the management software.

One important instance of such an occurrence would be in the aftermath of an automobile accident, where an injured party may have his/her medical information contained in a reproducible layer 110 embedded in a government-issued driver's license (the license, by way of example only, being the "subject" 150. In such a situation, a caregiver or medical professional may scan the injured subject's driver's license for critical information.

Once the medical professional receives the scanning signal, the scanner sends the signal to the management software 614, in particular EHR 613 or EMR 615 management software, if available. The EHR 613 or EMR 615 management software retrieves the identification information of the injured subject 150 from the received scan signal. The management software 613, 614, 615 may search in a corresponding database, based on the retrieved identification information of the injured subject 150, to find a unique record that matches or associates with the identification information of the injured subject 150. The unique record achieved than may be used to provide appropriate medical attention to the injured subject 150

Optionally, when the EHR or EMR management software 613,615 finds a matching record in the database, the EHR or EMR management software 613, 615 may return to the user with the information pertaining to the subject, and display or act upon the information. When the user is only allowed to view certain information per security policy in place of the EHR or EMR management software 613, 615 the EHR or EMR management software may 613,615 return to the user with only the information allowed under the security policy.

A further aspect of the present inventive concept relates to a system for identifying a subject. In certain embodiments, the system includes a temporary tattoo and a computer system. FIG. 6 shows schematically a system for identifying a subject according to one embodiment of the present invention. As shown in FIG. 6, the system 600 includes a computer system 610, and a TID 100 containing a reproducible layer 110 which may be positioned so as to adhere to the skin (or surface) of a subject 150. The reproducible layer 110 may be any temporary medium, as described above, which is incorporated into the TID 100.

As shown in FIG. 5, the computer system 600 includes a processor 612, management software 614, and a database 616, storing information pertaining to the subject. Further, the computer system 610 has a plurality of peripheral devices, such as a printing device 200 and an optical scanning device 210. In certain embodiments, the computer system 610 may include other hardware and/or software components which are deemed necessary for the operation of the computer system 610, such as one or more memory modules, one or more storage devices, interconnection interfaces and buses between the components, one or more input/output (I/O) devices, and one or more software application programs executable on the computer system 610.

The computer system 610 may be implemented by one or more computers. Examples of such computers applicable as, or to be a part of the computer system 610 may include, but not being limited to, desktop computers, laptop computers, and portable computing devices such as smartphones and tablets.

The processor 612 is a processing unit to control operation and to execute instructions of the computer system 610. The processor 612 may execute the software programs or applications of the computer system 610, such as generic management software 614, EHR software 613, or EMR software 615. The processor 612 may be a central processing unit (CPU).

The database 616 is a data store which stores information of the subject 150. In certain embodiments, the database 616 stores all information of a plurality of subjects which may be identifiable using the management software 614. For example, the database 616 may store all information of the patients in a particular hospital. The information of each patient includes the identification information of the patient, such that the management software 614 may use the identification information to search for matching records.

While preferred embodiments of the present inventive method have been shown and disclosed herein, it will be obvious to those persons skilled in the art that such embodiments are presented by way of example only, and not as a limitation to the scope of the inventive concept. Numerous variations, changes, and substitutions may occur or be suggested to those skilled in the art without departing from the intent, scope, and totality of this inventive concept. Accordingly, the scope of the present invention is defined by the appended claims rather than the foregoing description and the exemplary embodiments described therein.

What is claimed is:

1. A device for providing a temporary display of identification information of a tangible subject, the temporary identification device comprising a removable coating, a reproducible layer having an outer surface, and an interior surface, wherein one surface of the reproducible layer further contains, integrally, a pictographic rendering of data, information, and visualization codes specifically pertaining to the subject, such that the pictographic rendering contained on that surface is transferrable directly onto the exterior of the subject, without the removable coating also being transferred onto the subject.

2. The device of claim 1, wherein the interior surface of the reproducible layer manifests pictographic rendering of data, information, and visualization codes specifically pertaining to the subject.

3. The device of claim 1, wherein the interior surface of the reproducible layer manifests pictographic rendering of data, information, and visualization codes, and further, the interior surface of the reproducible layer is formed with a resistant, adhesive material, such that when pressure is applied to the outer surface against the subject, the data, information, and visualization codes are transferred directly onto the exterior of the subject, without the removable coating also being transferred onto the subject.

4. The device of claim 1, wherein the data, information, and visualization codes contained by the reproducible layer include name, age, gender, blood type, hospital unit, Quick Response code, and the overall health status of the subject.

5. The device of claim 1, wherein the pictographic rendering of data, information, and visualization codes on the reproducible layer comprises a resistant ink.

6. The device of claim 1, wherein the reproducible layer is dissolvable only in a chemical solvent such that the reducible layer is only removable from the subject using the chemical solvent.

7. The device of claim 1, wherein the visualization codes further comprise optical machine readable codes comprising at least one of a bar code and at least one of a quick response (QR) code.

8. The device of claim 1, wherein the data, information, and visualization codes of the reproducible layer are formed with a resistant ink.

9. The device of claim 1, wherein a transparent or translucent removable coating is affixed to the outer surface of the reproducible layer such that the data, information, and visualization codes of the reproducible layer are discernible through the removable coating.

10. The device of claim 1, wherein the data, information, and visualization codes are transferred onto the subject by:
   disposing the temporary identification device on the subject with the interior surface of the reproducible layer in direct contact with the subject;
   applying pressure to the removable coating of the temporary identification device such that the reproducible layer adheres onto the subject to form an impression or imprint of the data, information and visualization codes visualization codes directly on the surface of the subject; and
   detaching the removable coating from the reproducible layer.

11. A system for providing identification of a human or animate subject in a hospital, veterinary clinic, or other medical care facility, comprising:
   a device for providing a temporary display of identification information of the subject, the temporary identification device comprising a removable coating, a reproducible layer having an outer surface and an interior surface, wherein the interior surface of the reproducible layer further contains, integrally, a pictographic rendering of data, information, and visualization codes specifically pertaining to the subject, such that the pictographic rendering is transferrable onto the exterior of the subject without the removable coating also being transferred onto the subject;
   the reproducible layer being formed with a resistant material, such that the pictographic rendering of data, information, and visualization codes of the reproducible layer may adhere to the subject;
   a computer system having a processor, an optical scanning device, a printing device, management software and a database storing information pertaining to the subject, wherein the management software, when executed at the processor, is configured to perform the following operations:

(a) receive an input of the data, information, and visualization codes of the subject;
(b) generate the data, information, and visualization codes;
(c) control the printing device to print the data, information, and visualization codes onto the reproducible layer, in the form of a resistant ink, so as to form a temporary identification;
(d) control the optical scanning device to scan the reproducible layer on the subject and, similarly, to receive a corresponding scanning signal, wherein the received signal contains the identification information of the subject;
(e) retrieve the identification information from the received scanning signal; and
(f) search, based on the retrieved identification information on the subject, the database for verification of the information of the subject, and thereby identify the subject.

12. The system of claim 11, wherein the data, information, and visualization codes contained by the reproducible layer include name, age, gender, blood type, hospital unit, Quick Response code, and the overall health status of the subject.

13. The system of claim 11, wherein the pictographic rendering of data, information, and visualization codes on the interior surface of the reproducible layer comprises a resistant ink.

14. The system of claim 11, wherein the reproducible layer is dissolvable only in a chemical solvent such that the reducible layer is only removable from the subject using the chemical solvent.

15. The system of claim 11, wherein the visualization codes further comprise optical machine readable codes comprising at least one of a bar code and at least one of a quick response (QR) code.

16. The system of claim 11, wherein the data, information, and visualization codes of the reproducible layer are formed with a resistant ink, the imprint of which may be transferred directly onto the subject.

17. The system of claim 11, wherein a transparent or translucent removable coating is affixed to the outer surface of the reproducible layer such that the data, information, and visualization codes of the reproducible layer are discernible through the removable coating.

18. The system of claim 11, wherein the resistant material is dissolvable only in a chemical solvent such that the reproducible layer is only removable from the subject using the chemical solvent.

19. The system of claim 11, wherein the reproducible layer is disposed upon or within the surface of the material comprising a government-issued driver's license belonging to the subject.

20. A method for providing temporary identification of a human or animate subject in a hospital, veterinary clinic, or other medical care facility, comprising:
acquiring specific personal and medical data and information on the subject, formatting same, and electronically entering the data and information into a database of a computerized management system;
generating pictographic representations of the data and information and converting to visualization codes corresponding to the subject;
scanning and/or printing a display of the data, information, and visualization codes of the subject, upon or within a temporary identification device, the device comprising a removable coating, a reproducible layer having an outer surface and an interior surface, wherein the interior surface of the reproducible layer receives, in the form of a resistant ink, the printing of a pictographic rendering of data, information, and visualization codes specifically pertaining to the subject;
transferring the pictographic rendering of data, information, and visualization codes from the reproducible layer directly onto the subject, without the removable coating also being transferred onto the subject;
and
as necessary, subsequently scanning the reproducible layer and receiving or sending a corresponding scanning signal, which contains the pictographic rendering.

21. The method as in claim 20, wherein the data, information, and visualization codes contained by the reproducible layer include name, age, gender, blood type, hospital unit, Quick Response code, and the overall health status of the subject.

22. The method as in claim 20, wherein the pictographic rendering of data, information, and visualization codes on the interior surface of the reproducible layer comprises a resistant ink.

23. The method as in claim 20, wherein the reproducible layer is dissolvable only in a chemical solvent such that the interior surface of the reproducible layer is only removable from the subject using the chemical solvent.

24. The method as in claim 20, wherein the visualization codes further comprise optical machine readable codes comprising at least one of a bar code and at least one of a quick response (QR) code.

25. The method as in claim 20, wherein the data, information, and visualization codes of the reproducible layer are formed with a resistant ink, the imprint of which may be transferred directly onto the subject.

26. The method as in claim 20, wherein a transparent or translucent removable coating is affixed to the outer surface of the reproducible layer such that the data, information, and visualization codes of the reproducible layer are discernible through the removable coating.

27. The method as in claim 20, wherein the resistant material is dissolvable only in a chemical solvent such that the reproducible layer is only removable from the subject using the chemical solvent.

28. The method as in claim 20, wherein the reproducible layer is disposed upon or within the surface of the material comprising a government-issued driver's license belonging to the subject.

* * * * *